United States Patent [19]

Chou

[11] Patent Number: 5,206,157
[45] Date of Patent: Apr. 27, 1993

[54] PREPARATION OF N-SUBSTITUTED-2-MORPHOLONE

[75] Inventor: Kechia J. Chou, Wappingers Falls, N.Y.

[73] Assignee: Texaco Inc., White Plains, N.Y.

[21] Appl. No.: 250,052

[22] Filed: Sep. 28, 1988

[51] Int. Cl.$^5$ .................... C12P 17/14; C12N 1/00
[52] U.S. Cl. .................... 435/120; 435/822; 435/823
[58] Field of Search .............. 435/120, 822, 823, 117, 435/118, 128

[56] References Cited

U.S. PATENT DOCUMENTS 4,246,345  1/1981  Kinast et al. .................... 435/822 X

OTHER PUBLICATIONS

Ohta, H. et al. 1982. *J. Organic Chemistry*, vol. 47, pp. 2400-2404.

Ohta, H. et al. 1981. *Agric. Biol. Chem.*, vol. 45, pp. 1895-1896.

Jones, J. K. N. et al. 1961. *Canad. J. Chem.*, vol. 39, pp. 2400-2410.

Morrison, R. T., and Boyd, R. N. *Organic Chemistry*, Third Edition. Allyn and Bacon, Inc., Boston. p. 674.

Kersters, K., and DeLey, J. 1963. "The oxidation of glycols by acetic acid bacteria." *Biochimica et Biophysica Acta* vol. 71 pp. 311-331.

*Primary Examiner*—Richard A. Schwartz
*Assistant Examiner*—M. E. Mosher
*Attorney, Agent, or Firm*—James J. O'Loughlin; Carl G. Seutter

[57] ABSTRACT

N-substituted dialkanolamine may be converted to N-substituted-2-morpholone by the action of *Gluconobacter oxydan* ATCC #621 or *Gluconobacter roseus* IAM 1841.

8 Claims, No Drawings

PREPARATION OF N-SUBSTITUTED-2-MORPHOLONE

FIELD OF THE INVENTION

This invention relates to the preparation of N-substituted-2-morpholones.

BACKGROUND OF THE INVENTION

As is well known to those skilled in the art, morpholones are useful chemicals. They may be reacted with hydrocarbonyl halides to yield quaternary ammonium compounds which are useful as wetting agents, textile assistants, and germicidal ampholytic detergents. They may also be reacted with glycols to yield esters which react with diisocyanates to give polyurethanes.

Conventional chemical processes to prepare morpholones including N-substituted-2-morpholones, are unsatisfactory because of low yields, high production of side products which are difficult to remove, expensive reagents, and unfavorable reaction conditions including high temperature.

It is an object of this invention to provide a process for preparation of 2-morpholones such as N-substituted-2-morpholones. Other objects will be apparent to those skilled in the art.

STATEMENT OF THE INVENTION

In accordance with certain of its aspects, this invention is directed to a method of preparing a product 2-morpholone which comprises maintaining a reaction mixture containing as charge dialkanolamine

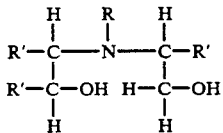

wherein R is alkyl, cycloalkyl, alkaryl, aralkyl, aryl, alkenyl, alkynyl or hydrogen and R' is alkyl, cycloalkyl, alkaryl, aralkyl, aryl, alkenyl, alkynyl or hydrogen;

adding to said reaction medium Gluconobacter or Acetobacter bacteria;

maintaining said reaction mixture at ring-forming conditions thereby forming product 2-morpholone

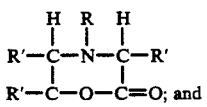

recovering said product 2-morpholone.

DESCRIPTION OF THE INVENTION

The charge dialkanolamines, including N-substituted dialkanolamines, which may be treated by the process may be characterized by the formula

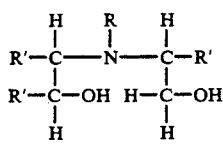

wherein R is alkyl, cycloalkyl, alkaryl, aralkyl, aryl, alkenyl, alkynyl or hydrogen and R' is alkyl, cycloalkyl, alkaryl, aralkyl, aryl, alkenyl, alkynyl or hydrogen.

In the above compound, R may be hydrogen or a hydrocarbon group selected from the group consisting of alkyl, aralkyl, cycloalkyl, aryl, and alkaryl, including such radicals when inertly substituted. When R is alkyl, it may typically be methyl, ethyl, n-propyl, iso-propyl, n-butyl, sec-butyl, amyl, octyl, decyl, octadecyl, etc. When R is aralkyl, it may typically be benzyl, beta-phenylethyl, etc. When R is cycloalkyl, it may typically be cyclohexyl, 3-methylcyclohexyl, etc. When R is aryl, it may typically be phenyl, naphthyl, etc. When R is alkaryl, it may typically be tolyl, xylyl, etc. When R is alkenyl, it may typically be vinyl, allyl, 1-butenyl, etc. When R is alkynyl, it may typically be ethynyl, propynyl, butynyl, etc. R may be inertly substituted i.e. it may bear a non-reactive substitutent such as alkyl, aryl, cycloalky, ether, etc. Typically inertly substituted R groups may include 2-ethoxyethyl, carboethoxymethyl, 4-methyl cyclohexyl, p-methylphenyl, p-ethylbenzyl, 3-ethyl-5-methylphenyl, etc. The preferred R groups may be lower alkyl, i.e. $C_1$-$C_{10}$ alkyl, groups including eg methyl, ethyl, n-propyl, i-propyl, butyls, amyls, hexyls, octyls, decyls, etc. R may preferably be methyl.

In the above compound, R' may be hydrogen or a hydrocarbon group selected from the group consisting of alkyl, aralkyl, cycloalkyl, aryl, and alkaryl, including such radicals when inertly substituted. When R' is alkyl, it may typically be methyl, ethyl, n-propyl, iso-propyl, n-butyl, i-butyl, sec-butyl, amyl, octyl, decyl, octadecyl, etc. When R' is aralkyl, it may typically be benzyl, beta-phenylethyl, etc. When R' is cycloalkyl, it may typically be cyclohexyl, cycloheptyl, cycloctyl, 2-methylcycloheptyl, 3-butylcyclohexyl, 3-methylcyclohexyl, etc. When R' is aryl, it may typically be phenyl, naphthyl, etc. When R' is alkaryl, it may typically be tolyl, xylyl, etc. When R is alkenyl, it may typically be vinyl, allyl, 1-butenyl, etc. When R is alkynyl, it may typically be ethynyl, propynyl, butynyl, etc. R' may inertly substituted i.e. it may bear a non-reactive substituent such as alkyl, aryl, cycloalkyl, ether, etc. Typically inertly substituted R' groups may include 2-ethoxyethyl, carboethoxymethyl, 4-methyl cyclohexyl, p-methylphenyl, p-ethylbenzyl, 3 ethyl-5-methylphenyl, etc. The preferred R' groups may be lower alkyl, i.e. $C_1$-$C_{10}$ alkyl, groups including eg methyl, ethyl, n-propyl, i-propyl, butyls, amyls, hexyls, octyls, decyls, etc. R' may preferably be hydrogen.

The charge dialkanolamine, including N-substituted dialkanolamine, may typically be the following, the first listed being preferred:

TABLE

| diethanolamine | |
|---|---|
| N-methyl | diethanolamine |
| N-ethyl | diethanolamine |
| N-propyl | diethanolamine |
| N-cyclohexyl | diethanolamine |
| N-phenyl | diethanolamine |
| N-allyl | diethanolamine |
| N-butyl | diethanolamine |
| N-amyl | diethanolamine |

In practice of the process of this invention, 0.1 to 15 parts, say 10 parts of charge dialkanolamine may be added to 100 parts of aqueous nutrient medium.

The aqueous nutrient medium includes 0.1-5 parts, say 1 part of a nutrient protein source typified by yeast extract, peptone, etc and 0.1-10 parts, say 2.5 parts of a carbon source typified by carbohydrates such as mannitol, glucose, mannose or sucrose.

There is added to the aqueous nutrient medium containing the charge dialkanolamine, 0.1-20 parts, say 10 parts of Gluconobacter or Acetobacter bacteria. Preferred Gluconobacter species include *Gluconobacter oxydan* ATCC #621 and *Gluconobacter roseus* IAM 1841 and *Gluconobacter suboxydans* and *Gluconobacter scleroideus* IAM 1842. Typical Acetobacter species may include *Acetobacter oxydans* and *Acetobacter mesoxydans*.

Reaction may be carried out at 20° C.-50° C., preferably 25° C.-30° C. The temperature may be ambient temperature. As the temperature approaches the freezing point (ca 0° C.) or the boiling point (ca 100° C.), the bacteria are inactivated; and accordingly it is preferred to carry out the reaction within the noted range. Reaction is carried out for 24-120 hours. Shorter reaction periods may give lower yields while longer reaction periods do not appear to provide any advantage.

It is a feature of the process of this invention that the pH need not be controlled as by addition of buffers. The "normal" pH of the solution may be determined by the reactants and the course of the reaction. Commonly the pH at the beginning of reaction may be 6-8 say 7; and that at the end may be 3-6, say 5.

The reaction must be carried out aerobically. It is more advantageous to take steps to provide air during the reaction.

At the conclusion of the reaction, work-up typically includes removal of the bacteria, as by centrifugation. The desired product is extracted, typically with methylene dichloride. High Pressure Liquid Chromatography (HPLC) indicates 100% conversion with formation of no side products.

It is a feature of the process of this invention that it makes possible the production of substantially 100% yield of product with no production of by-product in a simple reaction.

The product 2-morpholones may be characterized by the formula.

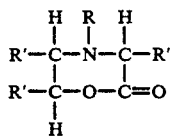

Typical products may include the following, the first listed being preferred:

TABLE

N-methyl-2-morpholone
N-ethyl-2-morpholone
N-propyl-2-morpholone
N-cyclohexyl-morpholone
N-phenyl-2-morpholone

DESCRIPTION OF PREFERRED EMBODIMENTS

Practice of this invention will be apparent to those skilled in the art from the following wherein as elsewhere in this specification, all parts are parts by weight unless otherwise stated.

EXAMPLE I

In this Example which sets forth the best mode presently known of practicing the process of this invention, there is added to a 250 ml flask 100 ml of aqueous nutrient medium containing 0.5 w % yeast extract, 0.5 w % peptone, and 2.5 w % mannitol. A loopful of *Gluconobacter oxydans* ATCC #621 (in nutrient) and 2 millimoles of charge N-methyl diethanolamine are added.

The reaction medium is maintained at 30° C. in a shaker bath for 48 hours. The bacteria cells are then removed by centrifugation. The liquid is contacted with methylene dichloride which extracts the product N-methyl-2-morpholone. High Pressure Liquid Chromatography (HPLC) indicates a 100% yield with no formation of side product.

EXAMPLE II

The procedure of Example I is followed using diethanolamine as charge and, as bacteria, *Gluconobacter oxydans* ATCC #621. Conversion, after 48 hours, to 2-morpholone is 100% as determined by HPLC.

Results comparable to those of Example I-II may be obtained if the charge is as follows:

TABLE

| EXAMPLE | CHARGE |
|---|---|
| III | N-ethyl diethanolamine |
| IV | N-propyl diethanolamine |
| V | N-cyclohexyl diethanolamine |
| VI | N-phenyl diethanolamine |
| VII | N-allyl diethanolamine |
| VIII | N-butyl diethanolamine |
| IX | N-amyl diethanolamine |

Results comparable to those of Example I-II may be obtained if the bacteria employed are

| Example | Bacteria |
|---|---|
| X | *Gluconobacter roseus* IAM 1841 |
| XI | *Gluconobacter suboxydans* |
| XII | *Gluconobacter scleroideus* IAM 1843 |
| XIII | *Acetobacter oxydans* |
| XIV | *Acetobacter mesoxydans* |

Although this invention has been illustrated by reference to specific embodiments, it will be apparent to those skilled in the art that various charges and modifications may be made which clearly fall within the scope of the invention.

I claim:

1. The method of preparing a product 2-morpholone which comprises
    maintaining a reaction mixture containing as charge dialkanolamine

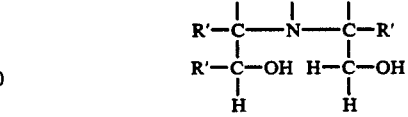

wherein R is alkyl, cycloalkyl, alkaryl, aralkyl, aryl, alkenyl, alkynyl, or hydrogen and R' is alkyl, cycloalkyl, alkaryl, aralkyl, aryl, alkenyl, alkynyl, or hydrogen;
adding to said reaction medium *Gluconobacter* or *Acetobacter* bacteria;

maintaining said reaction mixture at ring-forming conditions thereby forming product 2-morpholone

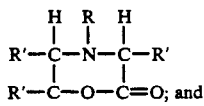

recovering said product 2-morpholone.

2. The method claimed in claim 1 wherein said charge dialkanolamine is diethanolamine.

3. The method claimed in claim 1 wherein said charge dialkanolamine is N-methyl diethanolamine.

4. The method claimed in claim 1 wherein said bacteria is *Gluconobacter oxydans* ATCC #621.

5. The method claimed in claim 1 wherein said bacteria is *Gluconobacter roseus* IAM #1841.

6. The method claimed in claim 1 wherein said reaction medium contains a nutrient protein source and a carbon source.

7. The method claimed in claim 1 wherein said reaction medium is maintained at 20° C.–50° C.

8. The method of preparing an N-substituted-2-morpholone which comprises maintaining a reaction mixture containing an N-substituted dialkanolamine

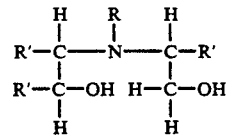

wherein R is alkyl, cycloalkyl, alkaryl, aralkyl, aryl, alkenyl, alkynyl or hydrogen and R' is alkyl, cycloalkyl, alkaryl, aralkyl, aryl, or hydrogen;

adding to said reaction medium bacteria selected from the group consisting of *Gluconobacter oxydan* ATCC #621 and *Gluconobacter roseus* IAM 1841;

maintaining said reaction mixture at ring-forming conditions thereby forming product N-substituted-2-morpholone

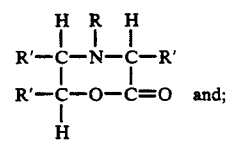

recovering said product N-substituted-2-morpholone.

* * * * *